US008622945B2

(12) United States Patent (10) Patent No.: US 8,622,945 B2
Meals (45) Date of Patent: Jan. 7, 2014

(54) SPRING LOADED ELBOW EXTENSION BRACE

(75) Inventor: Roy A. Meals, Los Angeles, CA (US)

(73) Assignee: Weber Orthopedic, Inc., Santa Paula, CA (US)

( * ) Notice: Subject to any disclaimer, the term of this patent is extended or adjusted under 35 U.S.C. 154(b) by 95 days.

(21) Appl. No.: 13/284,797

(22) Filed: Oct. 28, 2011

(65) Prior Publication Data

US 2013/0110022 A1  May 2, 2013

(51) Int. Cl.
  *A61F 5/00* (2006.01)
  *A61F 5/37* (2006.01)

(52) U.S. Cl.
  USPC .................................. 602/20; 128/878

(58) Field of Classification Search
  USPC ............... 602/5, 16, 20–21, 23–27, 62–66; 601/33–35; 128/845, 869, 878, 128/881–882; 2/16
  See application file for complete search history.

(56) References Cited

U.S. PATENT DOCUMENTS

| | | | | |
|---|---|---|---|---|
| 3,938,509 A | * | 2/1976 | Barber | 602/21 |
| 4,370,977 A | | 2/1983 | Mauldin et al. | |
| 4,665,905 A | * | 5/1987 | Brown | 602/16 |
| 5,038,764 A | * | 8/1991 | Paez | 602/22 |
| 5,312,322 A | * | 5/1994 | Santana | 602/20 |
| 5,403,002 A | * | 4/1995 | Brunty | 473/438 |
| 5,683,353 A | | 11/1997 | Hamersly | |
| 6,723,061 B2 | * | 4/2004 | Williams | 602/21 |
| 2002/0052568 A1 | | 5/2002 | Houser | |

\* cited by examiner

*Primary Examiner* — Patricia Bianco
*Assistant Examiner* — Ophelia A Hawthorne
(74) *Attorney, Agent, or Firm* — Paul Y. Feng; The Eclipse Group LLP

(57) ABSTRACT

An elbow brace worn by a patient to recuperate an injury to the ulnar nerve or "funny bone." The elbow brace includes two arched cuffs facing the same direction, and two struts interconnecting the cuffs. Each strut is formed from a wire of spring steel. A pair of oppositely-wound coiled springs are formed at about the middle of each strut. When worn, the patient's elbow is situated between the spring coils with the struts extending parallel to the arm, and one cuff resting against the mid upper arm and one cuff resting against the mid forearm. Two straps extend from respective coils of one strut to respective coils on the second strut. One strap fits underneath the forearm and the other strap fits underneath the upper arm. Each wire strut may be coated or covered by a tubular sheath or sleeve made of a soft polymer material.

20 Claims, 3 Drawing Sheets

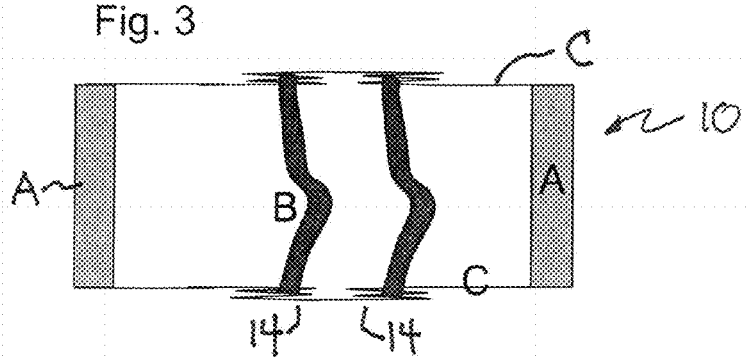
Fig. 3
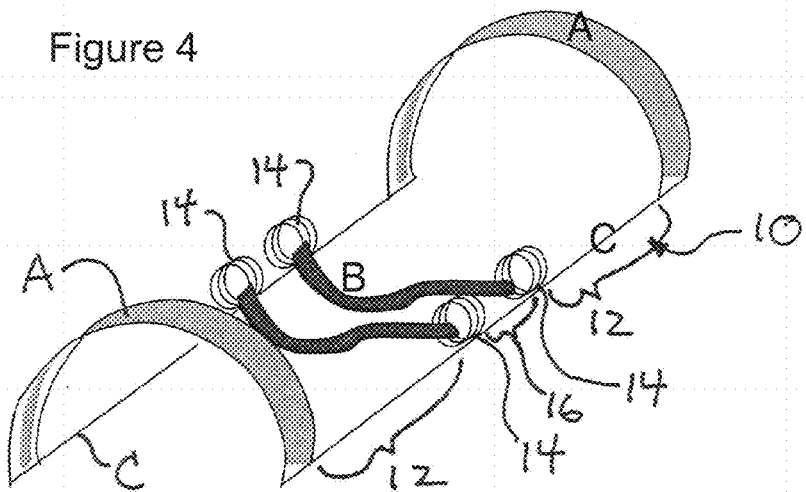
Figure 4
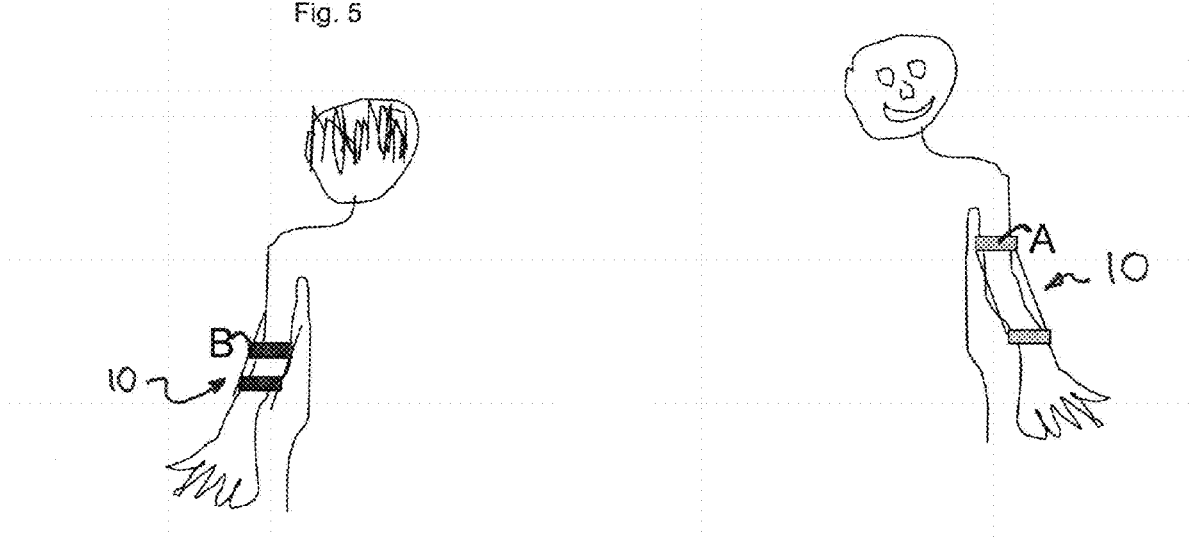
Fig. 5
Fig. 6

SPRING LOADED ELBOW EXTENSION BRACE

FIELD OF THE INVENTION

This present invention is directed to the field of medical devices for the treatment of disorders of the elbow and disorders of the ulnar nerve in the vicinity of the elbow.

BACKGROUND

Elbow braces are worn to immobilize, rest and protect the elbow joint itself as well as to rest and protect the ulnar nerve, colloquially known as the "funny bone," that passes from the upper arm to the forearm behind the elbow joint. The ulnar nerve supplies sensation to the small finger and half of the ring finger and supplies motor control to two muscles in the forearm and fifteen muscles in the hand. When the ulnar nerve becomes compressed at or near the elbow, numbness in the ring and small finger ensues along with weakness or paralysis of many of the muscles that control wrist and finger movements. Among other disabilities, the numbness precludes effective use of keyboards, because of inability to feel the keys with the small finger. Without the person having any tactile appreciation of an injury, burns and cuts can occur when the numbness is profound. Moreover, weakness of the muscles controlled by the ulnar nerve causes diminished grip and pinch strengths.

People with ulnar nerve compression thereby have difficulty with such tasks as opening jars and turning keys. Weakness in muscles controlled by the ulnar nerve also leads to loss of dexterity and coordination for small object manipulation, such as fastening buttons or manipulating paperclips.

The ulnar nerve passes behind the elbow in a bony groove which is covered by a fibrous sheet. The ulnar nerve in this area can become compressed by one or both of the following mechanisms: (1) Prolonged direct pressure on the nerve in or near the groove can squeeze away the nerve's blood supply, causing the nerve to stop functioning, at first temporarily, and over time, permanently. Pressure can come from resting the closed (flexed) or semi-closed elbow on hard surfaces such as armrests on chairs or in cars or on table or desk surfaces. (2) The other mechanism by which the ulnar nerve can become compressed is holding the elbow in its closed position for prolonged periods, such as when sleeping curled up or when holding a phone to one's ear. Either mechanism of compression leads to the condition known as cubital tunnel syndrome. Cubitus is Latin for elbow, and tunnel is the groove through which the ulnar nerve passes. One of the nicknames for cubital tunnel syndrome is "stock broker's elbow," where the person may be on the phone for prolonged periods and at the same time resting the closed elbow and the ulnar nerve on a hard desk surface.

The first steps of treatment for cubital tunnel syndrome are to diminish the time that the elbow is held in a closed position and to diminish the direct external pressure exerted on the nerve. Patients are advised to use a head set for their phone to preclude the prolonged closed-elbow position and to avoid resting their closed elbow on any hard surface.

Many people tend to curl into a fetal position during sleep and rest their hand(s) under their chin. This posture, of course, is quite natural but it applies undesirable pressure on the ulnar nerve overnight. This sleep posture is ingrained from before birth. It is a hard posture to avoid after falling to sleep even if the person consciously positions the elbow in a straight (extended) or nearly straight position before falling asleep. Various means of elbow immobilization have been devised to prevent the sleeping person from unwittingly assuming and sustaining the injurious closed-elbow position.

Elbow extension braces known in the art are typically cylindrical, perhaps with sections of the cylinder cut away, and cover the upper arm and forearm for variable distances above and below the elbow. A simple, homemade elbow extension brace is a bath towel first folded so that it is approximately as wide as the distance from the user's wrist to armpit, and then rolled around the limb with the ensuing, multi-layered cylinder being secured to itself with safety pins. At bedtime, the user slips this thick sleeve over the elbow. The bulk of the fabric and its proximity to the limb precludes the user from comfortably resting in an elbow-closed position.

Another improvisation uses a basketball knee pad slipped over the elbow with the pad portion on the side of the elbow readily visible when looking at one's own elbow (the front surface, the anterior surface). The bulk of the springy padding discourages prolong posturing in the elbow-closed position. Various commercial braces designed specifically for elbow extension and treatment of cubital tunnel syndrome are also available. These braces typically consist of fabric, which either through its own bulk or through the incorporation of rigid or semi-rigid strut(s), maintains its general cylindrical shape even of the user consciously or unconsciously tries to close the elbow. The brace is typically secured to the limb through portions of the fabric being elastic and thereby snugly conforming to the enclosed limb or through a means of straps secured by hook and loop fasteners or through both methods. At times, a hand therapist or orthotist custom-molds an elbow extension brace out of rigid or semi-rigid material and secures it to the user's elbow area with straps and fasteners.

The braces of the prior art suffer certain inadequacies. They cover the majority of the limb from armpit to wrist and prevent radiation of heat and evaporation of perspiration, thereby causing the limb to become hot and sweaty. Environmental dirt, perspiration, and body oils permeate and adhere to the brace fabric, raising both sanitation concerns and aesthetic concerns. The fabric portion of the brace is difficult to wash, especially if the rigid or semi-rigid struts are permanently attached or enclosed. The braces of the prior art frequently have elasticized fabric or strapping material pressing directly on the ulnar nerve behind the elbow, thereby contributing to the nerve irritation. The most glaring inadequacy of the braces of the prior art is that they do not allow even momentary closing (flexing) of the elbow should the wearer want to scratch his nose or adjust his pillow.

SUMMARY OF THE INVENTION

The present invention in a preferred embodiment is directed to an elbow brace adapted for rehabilitating a patient's elbow and worn on the mid forearm and mid upper arm, the elbow brace comprising two arched, semi-rigid, first and second cuffs, with the first cuff disposed on the mid forearm and the second cuff disposed the mid upper arm; generally parallel first and second struts connecting the first and second arched cuffs, wherein the first and second struts are situated respectively on the inside and the outside of the elbow, and wherein the cuffs and the struts form a rectangular shape; each of the first and second struts having a straight portion at each end and a series of torsion springs in between the straight portions that function as a flex point for the elbow brace, wherein the series of torsion springs are wound in clockwise and counterclockwise directions, and the series of torsion springs are generally coplanar; padding disposed on a concave surface of the first and second cuffs; and a first strap and a second strap extending from the first strut across to the second strut, wherein the first strap is disposed underneath the forearm and the second strap is disposed underneath the upper arm.

In various alternative embodiments, each strut further comprises a first end of the strut leading to the straight portion leading to two coiled torsion springs in series being wound in clockwise and counterclockwise fashion that extend to a short straight portion, that extends to another two coiled torsion springs in series being wound in clockwise and counterclockwise fashion, extending to another straight portion terminating at a second end of the strut. Each strut may be formed form a single, uninterrupted length of spring steel metal wire having a constant outside diameter from end-to-end. The spring coils may be arranged so their center axes are generally perpendicular to the respective longitudinal axes of the first and second struts.

Further, the elbow brace may have struts including the torsion springs that are at least partially covered by a soft, pliable coating, and/or a soft, pliable tubing that closely wraps the exterior of each strut and spring. The series of torsion springs of the first strut includes a first pair of oppositely wound torsion springs and a second pair of oppositely wound torsion springs.

Each cuff may have a semicircular shape formed of a semi-rigid polymer. Each strut may be formed from a single spring steel wire of a constant diameter. Further, the first and second struts and their respective coiled springs may be arranged to be coplanar when the brace is not being worn.

In still further alternative embodiments, the first and second straps are elastic, and the first and second cuffs have a concave shape and are facing the same direction to receive the wearer's arm. In each strut, the springs preferably have less bending rigidity than the straight portions such that they may function as a flex point for the elbow brace when the patient flexes the elbow. In the wire used to form the strut, the wire preferably has a constant bending stiffness from end-to-end.

BRIEF DESCRIPTION OF THE DRAWINGS

The present invention will be understood and appreciated more fully from the following detailed description, taken in conjunction with the drawings in which:

FIG. 3 is an anterior-posterior view of the elbow brace.

FIG. 4 is a perspective view.

FIG. 5 is a posterior view of the elbow brace worn by a patient.

FIG. 6 is an anterior view of the elbow brace worn by a patient.

Figure 1:
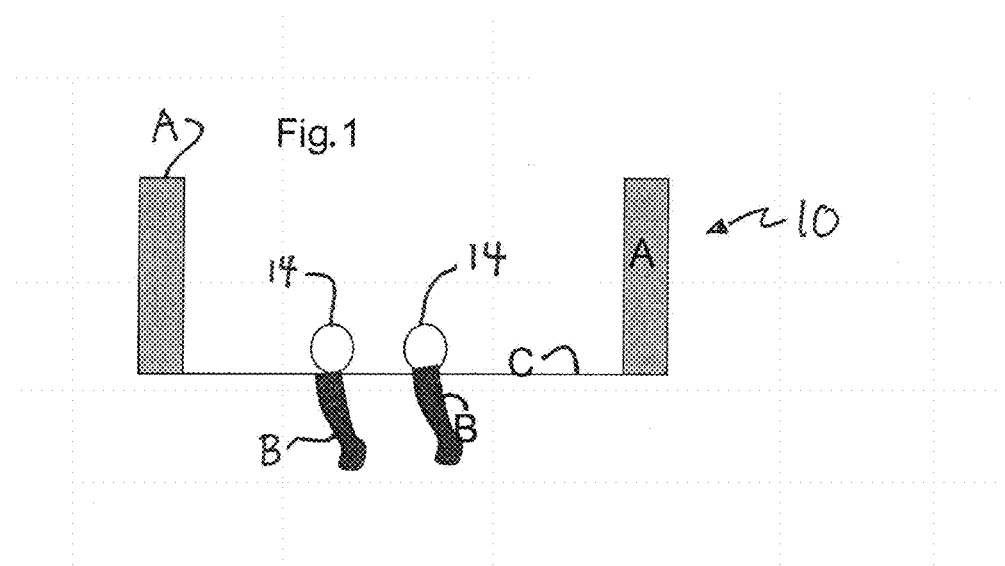
FIG. 1 is a side elevational view of a preferred embodiment elbow brace.
Figure 2:
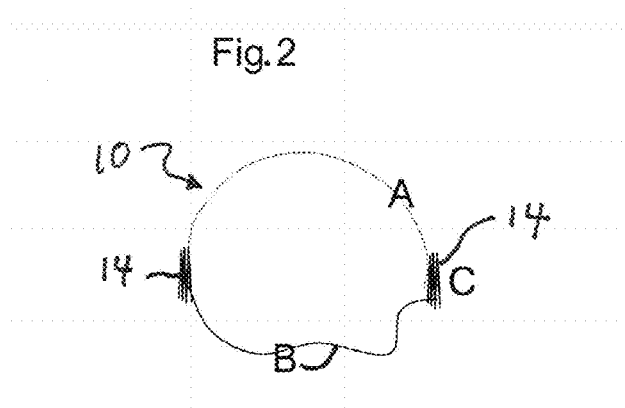
FIG. 2 is an end view of the elbow brace from FIG. 1.

It will be appreciated by persons skilled in the art that the present invention is not limited by what has been particularly shown and described hereinabove. Rather, the scope of the present invention includes both combinations and subcombinations of the various features described hereinabove, as well as modifications and variations thereof which would occur to a person of ordinary skill in the art upon reading the following description and which are not in the prior art.

DETAILED DESCRIPTION OF THE PREFERRED EMBODIMENTS

The present invention in a preferred embodiment is directed to an elbow brace 10 as illustrated in schematic form in FIGS. 1-6. FIGS. 1-6 provide various views of the elbow brace 10 and FIGS. 5 and 6 show the elbow brace as worn by a patient.

The preferred embodiment elbow brace 10 has two arched, roughly semicircular, cuffs A, one straddling the mid forearm and the other straddling the mid upper arm, and connected to one another by straight struts C made of spring steel wires on both the inside and the outside of the elbow. The struts C are generally parallel to each other. Looking directly from an anterior-posterior view (FIG. 3), with the brace 10 in place on the patient's arm, the brace 10 makes a generally rectangular shape with the cuffs A forming the short ends of the rectangle and the spring steel wire struts C forming the long sides of the rectangle.

The arched cuffs A are made of semi-rigid material and are optionally covered with fabric or have a gel material on their concave surface for comfortable contact with the wearer's skin. The concave sides of the cuffs A face the same direction. The cuffs A are preferably formed from a semi-rigid polymer, such as polyethylene, nylon, polycarbonate, polypropylene, or the like. A metal such as aluminum may be used to reinforce or form the cuff as well. The fabric or padding is preferably stitched around the periphery to partially or fully cover the cuff A.

As seen in FIG. 4, each spring steel wire strut C that secures the arched cuffs A to one another has straight portions 12 near its ends separated by two torsion springs 14 arranged in series. The torsion springs 14 provide bias into the brace 10 so that when it is flexed by the wearer, the springs resist the flexing, and further provide one or more flex points in the brace. The torsion springs 14 are separated or spaced apart a short distance from one another and are preferably coplanar. The coplanar springs 14 act in unison when the brace is flexed by the patient; if the springs were not coplanar, there may be distortion and skewed forces acting on the springs, reducing their biasing efficiency in the brace. There is an optional straight portion 16 between the springs 14 to space them apart. This space between the springs 14 is where the patient's elbow is located.

Each strut C is preferably made from a single, continuous, uninterrupted, constant diameter strand of spring steel wire having the same mechanical properties from end-to-end. This same wire is preferably used to form the springs 14. When coiled into a spring, the bending stiffness at the springs 14 is lower than at the straight portions 12, 16. When worn by a patient who flexes his elbow, the majority of the bending occurs at one or more of the springs 14, with some lesser flexing at the straight portions 12, 16. Thus, there is no need for hinges or pivot points that would be otherwise necessary for the elbow brace to fully flex. In various alternative embodiments, the spring steel wire used for the struts and springs may have different diameters or bending stiffness. For example, if more rigid struts are needed (as compared to the springs), then the diameter at the struts can be increased relative to the diameter of the section of the wire used for the coils of the springs. Or if more flexible springs are needed, then that section of the wire may be locally heat-treated, or their diameter reduced, or a combination thereof.

One torsion spring 14 in each steel wire strut C is preferably wound clockwise and the other is wound counterclockwise for maximum effectiveness of the torsion springs. Each spring has most preferably two turns per coil, but one turn and three or more turns are contemplated. Too many turns on a spring increases the profile and bulkiness of the brace, which may not be desirable. The pairs of springs may alternatively be wound in the same direction. As best seen in the plan view of FIG. 3, each spring 14 has coiled turns that have a center axis which is generally perpendicular to the longitudinal axis of the strut C. This preferred alignment of the springs relative to the strut is found most effective in resisting and forcing the bent strut back to its straight, unbent condition.

The spring steel wire struts C are permanently affixed at their ends to the cuffs A. The steel wires struts C including the torsion springs 14 are preferably entirely covered by soft rubber tubing or other similar coating that provides a soft, pressure-distributing contact with the wearer's skin. The tubing, sleeve, sheath, or coating is preferably a soft and flexible thermoplastic or elastomeric material. The tubing or coating runs coaxially along generally the entire length of the strut C including each turn of the coils in each spring. The coating or tubing prevents hair from becoming pinched within the spring coils 14 and minimizes any potential abrasive effects on the wearer's skin.

When the brace 10 is worn by the patient on his or her arm, one torsion spring 14 in each steel wire strut C is located slightly above the elbow adjacent to the upper arm and the other slightly below the elbow adjacent to the forearm. An optional fastening strap B runs through the upper arm coil 14 on one long side of the rectangle to and through the upper arm coil 14 on the other long side of the rectangle. A similar fastening strap B runs the same course between the two coils 14 situated adjacent to the forearm. As seen in FIG. 5, looking at the elbow in a posterior to anterior direction with the brace in place, one fastening strap B crosses the posterior aspect of the upper arm and the other fastening strap crossing the posterior aspect of the forearm. The pivot point of the patient's elbow is positioned in between the two straps B as is the ulnar nerve as it passes through the cubital canal. In other words, no portion of the brace 10, and no padding or fabric material, covers the ulnar nerve or exerts pressure on it in the cubital tunnel. No pressure exerted by the brace 10 on the damaged ulnar nerve means comfort for the patient, and little likelihood of inflicting further injury.

With the brace in place, the elbow is supported in a straight (extended) position and the straps B and cuffs A produce only minimal pressure against the patient's skin. The straps B may be elastic for better fitment on the patient's arm. They preferably pass through the turns of the springs 14 and are anchored to the springs 14. Each strap B may have a length adjustment via hook-and-loop fasteners, snaps, or the like.

If the wearer closes (flexes) the elbow, the torsion springs 14 are sufficiently strong that they resist but do not prevent flexion of the elbow. Once the wearer relaxes the muscles (principally the biceps muscle) that closes the elbow, the torsion springs 14 bias the struts C and the enclosed elbow to a fully or nearly fully straightened position. By this means the wearer can momentarily close his elbow to use his hand in a full range of elbow motion, but he will be reminded by the opposing pressure exerted by the brace 10 to return the elbow to a resting, straightened position. Likewise, even if the wearer is asleep and involuntarily closes his elbow, the spring-loaded brace will urge it back into a straightened position. Therefore, during sleep, the elbow will be generally maintained in a straight position and minimize pressure on the ulnar nerve. Hence healing to the elbow is enhanced and time to recuperate is shortened.

Furthermore, the present invention elbow brace does not require padding, liners, hinges, a rigid shell, or large swatches of support fabric so that it has an essentially a skeletal construction. As such, the present invention brace is light weight and has a low profile with minimal limb contact for comfort of the wearer, especially when sleeping. The use of the spring steel wire in the struts and coiled springs enable the brace to be highly flexible. The low profile, flexible elbow brace is thus unobtrusive when worn, allowing the patient to perform routine activities with very little restriction.

Figure 7:
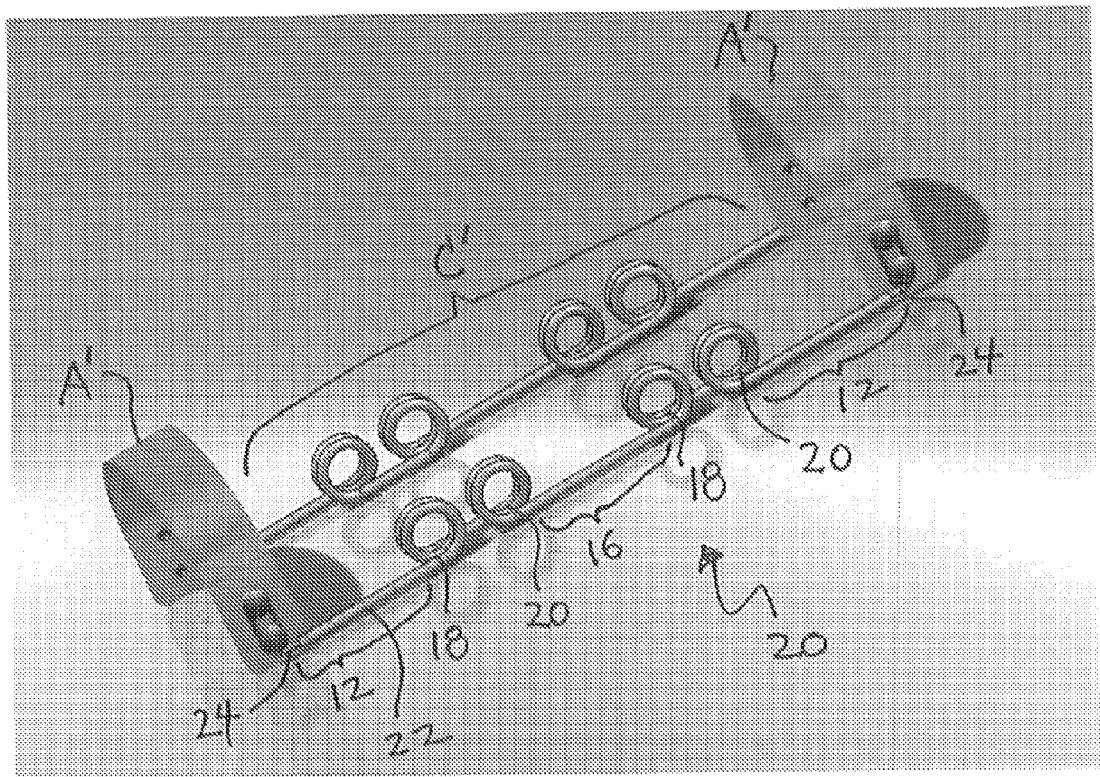
FIG. 7 is a perspective view of an alternative embodiment elbow brace.

FIG. 7 is a perspective view of an alternative embodiment elbow brace 20. The elbow brace 20 includes a cuffs A' at each end and struts C' that interconnect the cuffs A' to generally form a rectangular shape (as seen from a plan view or anterior-posterior view). Each strut C' includes straight portions 12 connected to the cuffs A' and two pairs of oppositely coiled springs 18, 20, with a straight portion 16 spacing out the pairs of springs.

In the embodiment shown, the cuffs A' are made of a flexible, semi-rigid polymer material. In this embodiment, they are not covered by fabric. The ends of the struts C' are riveted to the cuffs A' where the wire ends of each strut C' is bent to wrap around the shaft of each rivet. Other means for joining the strut ends to the cuffs can be used, including a mechanical lock, an friction fit joint, a hook, chemical bonding, screws, welding the polymer cuff to the wire, or the like.

In this embodiment, as shown in the unworn, unflexed state, the struts C' including the coiled springs 18, 20 all fall within a common plane. Each strut C' is preferably made from a single, continuous, uninterrupted, constant diameter strand of spring steel wire 24 having the same mechanical properties from end-to-end. When coiled into a spring, the bending stiffness at the coils 18, 20 is lower than at the straight portions 12, 16. When worn by a patient as in FIGS. 5, 6, when the patient bends or flexes his or her elbow, the majority of the flexing in each strut occurs at the springs 18, 20 with lesser flexing at the straight portions 12, 16. Accordingly, there is no need for a pivot or hinge for struts C' to enable elbow bending by the patient.

The FIG. 7 embodiment includes a tubular sheath 22 that coaxially covers the entire strut C' including the coils 18, 20, with only the ends of the wire 24 exposed. Thus, the sheath 22 follows each turn of each coil 18, 20, and the sheath diameter closely matches the wire diameter although the sheath preferably is still loosely fitted over the wire 24. As mentioned above, the sheath (or coating if any) minimizes the coiled springs from pinching or catching the wearers arm hair or skin, and minimizes discomfort from the strut C' possibly abrading or scraping the wearer's skin as the elbow brace undergoes flexing or straightening. Alternatively, the sheath may cover the turns of the spring coils in their entirety, i.e., not coaxially or following each turn (not shown).

From the foregoing detailed description, it should be evident that there are a number of changes, adaptations and modifications of the present invention that come within the province of those skilled in the art. Features or structures of one embodiment may be combined with features or structures in another embodiment. However, it is intended that all such variations not departing from the spirit of the invention be considered as within the scope thereof except as limited solely by the following claims.

I claim:

1. An elbow brace adapted for rehabilitating a patient's elbow and configured to be worn on the mid forearm and mid upper arm, the elbow brace comprising:

two arched, semi-rigid, first and second cuffs, with the first cuff configured to be disposed on the mid forearm and the second cuff configured to be disposed the mid upper arm;

generally parallel first and second struts connecting the first and second arched cuffs, wherein the first and second struts are configured to be situated respectively on the inside and the outside of the elbow, and wherein the cuffs and the struts form a rectangular shape;

each of the first and second struts having a longitudinal axis including a straight portion at each end and a series of torsion springs in between the straight portions that function as a flex point, wherein the series of torsion springs are wound in clockwise and counterclockwise directions, and the series of torsion springs are generally coplanar;

padding disposed on a concave surface of the first and second cuffs; and a first strap and a second strap extending from the first strut across to the second strut, wherein the first strap is configured to be disposed underneath the forearm and the second strap is configured to be disposed underneath the upper arm.

2. The elbow brace of claim 1, wherein each strut further comprises a first end of the strut leading to the straight portion leading to two coiled torsion springs in series being wound in clockwise and counterclockwise fashion that extend to a short straight portion, that extends to another two coiled torsion springs in series being wound in clockwise and counterclockwise fashion, extending to another straight portion terminating at a second end of the strut.

3. The elbow brace of claim 2, wherein each strut is formed from a single, uninterrupted length of spring steel metal wire.

4. The elbow brace of claim 2, wherein the series of torsion springs includes respective coils with center axes and the coils are arranged so the center axes are generally perpendicular to the respective longitudinal axes of the first and second struts.

5. The elbow brace of claim 1, wherein the struts including the torsion springs are at least partially covered by one of a soft, pliable coating and a soft, pliable tubing material.

6. The elbow brace of claim 1, wherein the series of torsion springs of the first strut includes a first pair of oppositely wound torsion springs and a second pair of oppositely wound torsion springs.

7. The elbow brace of claim 1, wherein the cuffs have a semicircular shape formed of a semi-rigid polymer.

8. The elbow brace of claim 1, wherein each strut is formed from a single spring steel wire of a constant diameter.

9. The elbow brace of claim 1, wherein the first and second struts and the series of torsion springs are generally coplanar when the brace is not being worn.

10. An elbow brace configured to be worn by a patient for rehabilitating the elbow, the elbow brace comprising:

first and second cuffs each having an arch, arranged with the respective arches facing the same direction;

first and second struts connecting the first and second arched cuffs;

the first strut having a straight portion leading to a first pair of oppositely-wound springs leading to a second pair of oppositely-wound springs and leading to another straight portion;

the second strut having a straight portion leading to a first pair of oppositely-wound springs leading to a second pair of oppositely-wound springs and leading to another straight portion;

wherein the first and second struts and the respective first and second pairs of oppositely-wound springs are all generally coplanar when not being worn, and at least one pair of oppositely-wound springs act as a flex point;

wherein the straight portions of the first and second struts are connected to the first and second cuffs to form a generally rectangular shape;

means for covering the first and second struts and pairs of oppositely-wound springs with a soft material;

a first strap extending from the first strut to the second strut and anchored at opposite ends on the oppositely-wound springs of the respective struts;

a second strap extending from the first strut to the second strut and anchored at opposite ends on the oppositely-wound springs of the respective struts; and wherein the first and second straps are configured to be positioned at opposite sides of the elbow.

11. The elbow brace of claim 10, wherein each strut includes a continuous length of spring steel wire having a constant diameter from end-to-end and formed into straight portions and oppositely-wound springs.

12. The elbow brace of claim 11, wherein the continuous length of spring steel wire has a constant bending stiffness from end-to-end.

13. The elbow brace of claim 10, wherein the first and second straps are elastic.

14. The elbow brace of claim 10, wherein the first and second cuffs have a concave shape and are facing the same direction.

15. The elbow brace of claim 10, wherein in each strut the oppositely-wound springs have less bending rigidity than the straight portions.

16. An elbow brace configured to be worn by a patient for rehabilitating the elbow, the elbow brace comprising:

two arched, first and second cuffs arranged with the cuffs facing the same direction;

first and second struts connecting the first and second arched cuffs;

the first strut having a straight portion leading to a first pair of oppositely-wound springs that are spaced apart from a second pair of oppositely-wound springs that lead to another straight portion;

the second strut having a straight portion leading to a first pair of oppositely-wound springs that are spaced apart from a second pair of oppositely-wound springs that lead to another straight portion, and wherein the elbow is configured to be located in between the first and second pairs of the oppositely-wound springs of the first and second struts, and at least one of the first and second pairs of oppositely-wound springs functions as a flex point;

wherein the straight portions of the first and second struts are connected to the first and second cuffs to form a generally rectangular shape;

at least one of a soft coating and a closely-wrapped soft sheath covering the first and second struts;

a first strap extending from the first strut to the second strut and anchored at opposite ends on the oppositely-wound springs of the respective struts; and a second strap extending from the first strut to the second strut and anchored at opposite ends on the oppositely-wound springs of the respective struts.

17. The elbow brace of claim 16, wherein the first and second struts and their respective oppositely-wound springs are all coplanar when the brace is not being worn.

18. The elbow brace of claim 16, wherein the first and second straps pass through the oppositely-wound springs and attach thereto by hook-and-loop fasteners.

19. The elbow brace of claim 16, wherein the first strut and oppositely-wound springs are fabricated from a single strand of spring steel.

20. The elbow brace of claim 16, wherein the at least one of the soft coating and the closely-wrapped soft sheath covers the oppositely-wound springs and straight portions of the first and second struts.

* * * * *